Figure 1:
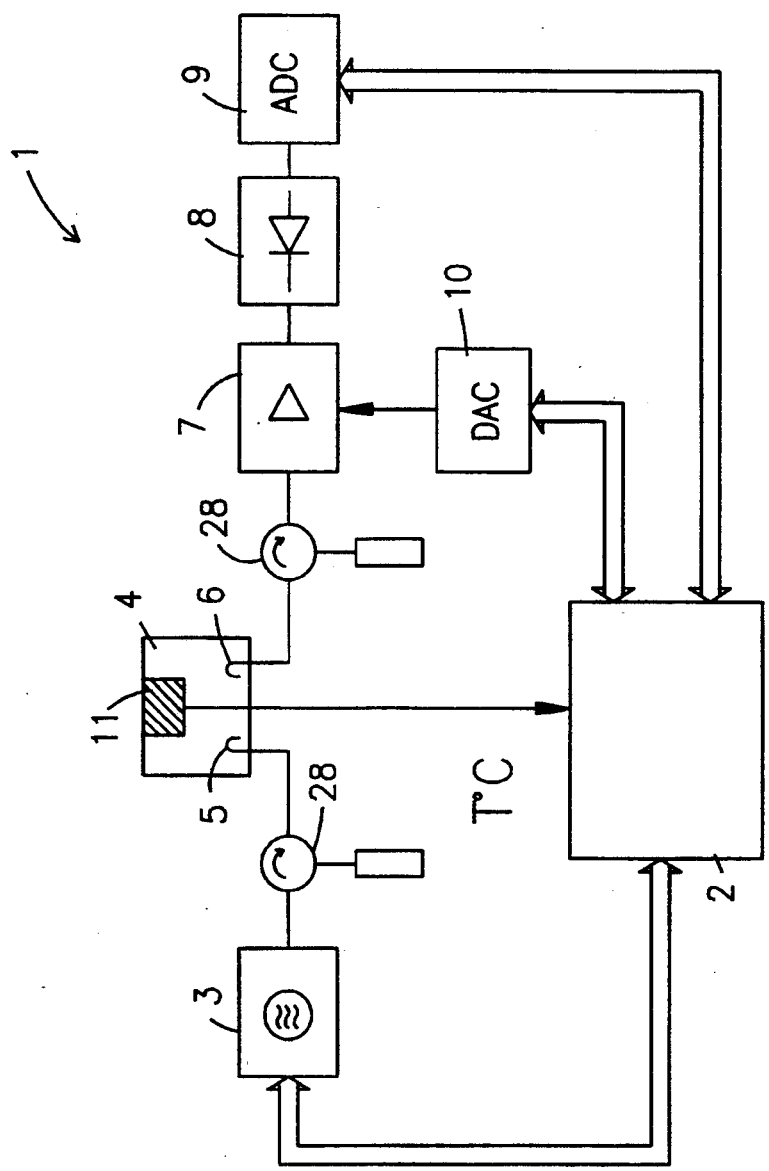

United States Patent [19]

Tews et al.

[11] Patent Number: 5,397,993
[45] Date of Patent: Mar. 14, 1995

[54] METHOD FOR MEASURING THE MATERIAL MOISTURE CONTENT OF A MATERIAL UNDER TEST USING MICROWAVES

[76] Inventors: Manfred Tews, Sperberhorst 10; Jan Sikora, Brodermannsweg 72, both of 2000 Hamburg 61; Rainer Herrmann, Kittwitzstrasse 15, 2000 Hamburg 20, all of Germany

[21] Appl. No.: 227,704

[22] Filed: Apr. 14, 1994

Related U.S. Application Data

[63] Continuation of Ser. No. 768,731, Dec. 9, 1991, abandoned.

[30] Foreign Application Priority Data

Feb. 10, 1990 [DE] Germany .............. 40 04 119.0

[51] Int. Cl.⁶ ........................... G01N 22/04
[52] U.S. Cl. .................... 324/634; 324/636; 324/632; 324/601; 324/643; 314/653; 314/310
[58] Field of Search ............... 324/634, 601, 632, 636, 324/653, 317, 310, 308

[56] References Cited

U.S. PATENT DOCUMENTS

| | | |
|---|---|---|
| 4,155,035 | 5/1979 | Fitzky . |
| 4,297,874 | 11/1981 | Sasaki .................. 324/631 |
| 4,581,575 | 4/1986 | Usaki .................... 324/631 |
| 4,885,527 | 12/1989 | Lacombe ............... 324/636 |

FOREIGN PATENT DOCUMENTS

| | | |
|---|---|---|
| 0372992 | 6/1990 | European Pat. Off. . |
| 2340130 | 12/1978 | Germany . |
| 2848993 | 5/1980 | Germany . |

OTHER PUBLICATIONS deJongh, "Moisture Measurement with Microwaves", Mikrowellen & HF Magazin, vol. 15, No. 8, 1989.
Mauer, "Digitalization and Automation of a Millimeter-Wave Spectrometer", Technisches, tm 56 (1989).
Fitzky, "Feuchtemessungen in Festkorpen, Flussigkeiten und Gasen mit Mikrowellen Verfahren zur Produktkontrolle fur Labor under Betrieb", pp. 869–880, 1974.

Primary Examiner—Kenneth A. Wieder
Assistant Examiner—Jose M. Solis
Attorney, Agent, or Firm—Dominik, Stein, Saccocio, Resse, Colitz & Van Der Wall

[57] ABSTRACT

A process and a device for determining the moisture content of the material of a test object using microwaves. The properties of a resonator such as resonance frequency, resonance half-width value and amplitude of the resonance can be measured using a digitally tunable quartz-stable PLL-controlled microwave generator. By special processing of the variations in the results due to detuning of the resonator when it is being filled with a product, the moisture content of the material in the product can be measured exactly, independently of the density of the material and largely independently of the type of material and of changes in additives. The same measurement equipment can be used, without any rearrangement of the hardware, both in the ppm range and up to moisture contents greater than 80%. In addition, there are no special requirements concerning the shape of the sample.

14 Claims, 15 Drawing Sheets

*Fig. 5a*  *Fig. 5b*

CLASSES OF COCOA
□ CLASS NO.1
○ CLASS NO.2
∗ CLASS NO.3
HAVING DIFFERING
SUGAR CONTENT

METHOD FOR MEASURING THE MATERIAL MOISTURE CONTENT OF A MATERIAL UNDER TEST USING MICROWAVES

This is continuation of application Ser. No. 07/768,731 filed on Dec. 9, 1991, now abandoned.

The invention relates to a process for measuring the material moisture content of a material under test using microwaves, in which process, under the control of a processor, an electromagnetic radiation of variable frequency is generated in a microwave generator and is fed to a sample applicator designed as a resonator, and in which the microwave signal emerging from the applicator is fed to a detector diode, from the signals of which b(0) and f(0) are determined as primary process variables by the computer via an analog/digital converter, where b(0) is the resonance half-maximum valve at the resonance frequency f(0) of the applicator which is operatively connected to a test sample, and to a device for carrying out the process.

In numerous industrial technical processes, the precise awareness of the moisture content of the materials subjected to the technical process is of great importance. Only if precise information on the material moisture content of the bulk materials, foodstuff products, pastes etc. is immediately available can regulatory action be taken with regard to the parameters of the production process. In many cases, this directly determines the desired improvement of the product quality, of the product stability and of the energyoptimal utilization of the process plant.

Accordingly, the most widely varying measurement methods for determining the moisture content of substances have already been proposed, these methods being based on conductivity measurement, capacitance measurement, infrared measurement, measurement in accordance with the neutron scattering process and the like. However, these processes have the most widely varying disadvantages, which restrict their applicability. Various processes are also known in which the moisture content of a substance is to be determined using microwaves. These processes are based, in the form of reflection, radiation transmission or resonance processes, on the high dielectric constant and the high loss factor of water. Resonance processes are also known for measuring the moisture content of a material under test using microwaves. In this case, the material under test, which is known per se, is subjected to measurement in an applicator which is known in terms of its mechanical and electrical properties and which is designed as a resonator. A prerequisite for the measurement is the plotting of a calibration curve, for which purpose the material under test is measured at differing known degrees of moisture content. The disadvantage of these known microwave processes consists in that in most cases they require, at the same time as the measurement of moisture content, a measurement of the density of the material using other measurement processes such as weighing and the like, in order to exclude the disturbing influencing of the microwave signals by density fluctuations. Hitherto known density-independent microwave processes for the measurement of moisture content exhibit the great disadvantage that they can be used only with a limited number of materials and within a narrow range of material moisture content, require precalibrations and postcalibrations or cannot be calibrated in situ under process conditions. Accordingly, there are serious restrictions when using hitherto known processes as regards application for measurement of moisture content in the case of industrial processes.

A process of the initially mentioned type is described in the periodical "Microwave Power", vol. 15, No. 8, 1989, pp. 648–649. In the case of this process there is, however, the disadvantage that the generator frequency is not adjustable. It is necessary to file in the computer a curve which associates the drive voltage of the VCO with the microwave frequency of the VCO. However, this brings about only a coarse linkage of generator frequencies and drive voltage, since this relation has been subjected to unceasing alterations due to generator load, temperature, aging and the like. According to this process, the resonance frequency changes and width changes can be detected only very roughly. The consequence of this is that a long-term-stable calibration of the system with linkage of the measurement signal A and the material moisture content or a fairly precise recording of the resonant frequencies and widths is not possible. Furthermore, this process is suitable only for the measurement of material samples of low moisture content values. The reason for this is that in order to obtain a certain separation of moisture content influence and density influence use is made of an expression as was already known from DE-A-2,928,487. At all events, this process is suitable to be able to measure on a density-independent basis as well, in a few specific practical applications involving low moisture content values, as long as the density fluctuations remain only within the range of small density values; in this case, only low degrees of resonator disturbance occur. If, on the other hand, the intention is to cover relatively large resonator disturbances, it must also be possible to undertake the precise measurement of resonant frequency and width; this is impossible on the basis of the known process.

Further, the periodical "G-I-T Fachzeitschrift für das Laboratorium", vol. 18, September 1974, contains a description of a measuring arrangement by means of which the microwave frequency is varied within a large range by altering the drive voltage of the microwave generator (VCO), without knowing the precise relation between drive voltage and generator frequency, which is dependent upon age, class, output load and temperature of the microwave generator. Accordingly, the resonator output signal is also scanned by the detector diode only for the maximum value which is achieved on passing through the resonant frequency. Thus, this system can measure only the resonance amplitude of the filled resonator in comparison with the resonance amplitude of the empty resonator. However, this attenuation measurement is just as sensitive to the packing density as to the material moisture content. Accordingly, this process can be used to measure the material moisture content only at locations where the packing density remains constant. Moisture content alterations and density alterations cannot be separated by this method. For this reason, this system has not entered into widespread use.

The object of the invention consists in improving a process of the initially mentioned type so that by means of a device suitable for this purpose the material moisture content in industrial processes can be measured with great accuracy, without the existence of a metrological dependence upon the density of the material or the class of material; in this case, the density of the material is at the same time to be measurable by evaluation of the microwave signal, independently of the respective moisture content. At the same time, the influence of the class of material, the moisture content of which is to be determined, on the microwave signal is to be reduced so that in the event of fluctuations in the chemical composition of the material it is not necessary to plot a new calibration curve.

According to the process according to the invention, it is possible to be able to measure the material moisture content using a microwave resonator process within the entire moisture content ranges occurring in industrial processes. The same measuring system can be used without any hardware conversion whatsoever on one occasion in the PPM range and next time up to moisture content values in excess of 80%. In each case of measurement, the density has no influence within the range from loose bulk up to maximum pressure. No special requirements are imposed on the form of the sample.

The resonance width is taken into consideration via the resonance frequency as a function of the packing density. Accordingly, the measurement signal $\Phi$ is the gradient of the straight line which describes the resonance width-frequency measurement points when the packing density, but not the moisture content of the material in the resonator is altered. The moisture-content-dependent measurement signal $\Phi$ can also be measured without knowing the properties of the empty resonator. To this end, the width-frequency values are measured under differing density conditions of a test sample in the resonator and are stored. Following this, the regression line is determined arithmetically, and the value of the gradient of the straight line of the moisture-content-dependent measurement value is established and the moisture content value is determined by means of the calibration curve. This mode of operation of the system permits measurements without any necessity to measure the empty resonator. The only requirement is for multiple measurements on the same product and with the same moisture content in differing density conditions.

This is readily possible when using many compressible products.

It is also possible to measure samples in the case of which the straight lines of constant moisture content or of differing density do not intersect one another at a point. This is so because if, on the other hand, the gradient $\Phi$ of the straight line of constant moisture content in the width-frequency diagram is determined by differing compression conditions, the measurement signal $\Phi$ continues to be strictly density-independent.

In contrast to known microwave measurement processes, the process according to the invention can also be employed in circumstances in which the empty condition of the resonator is unceasingly altering such as, for example, in the case of intense contaminations by the product. Furthermore, empty resonance measurements are not possible if the product extends in a strand.

The use of the device according to the invention can take place in the sample removal process or directly in the industrial process; in this case, the measurement process is distinguished by the following advantages:
the reproducibility and accuracy of the measurement on the unaltered product are increased. The limit of the accuracy of measurement is thus substantiated only by the quality of the comparative measurement which forms the basis of the measurement process in the form of a calibration curve.

The plotting of a calibration curve is possible directly in the process, under the conditions of the use of the device, with the simplest possible operation. A precalibration or postcalibration is dispensed with.

Following commencement of the measurement, the measurement result is available in the shortest possible time for the process control (measurement time as a rule approximately 1 s).

An alteration of the material density at constant material moisture content—for example by pressing or swelling of the material, or by alteration of the grain size, etc.—has no influence on the measurement signal. The measurement process is density-independent; it is dependent only upon the material moisture content. Accordingly, a separate process for measuring the density is also superfluous, such a process being customary when using devices of the type described, for example, by simultaneous weighing of the material under test, by requiring a defined filling volume or by radiometric methods.

An alteration of the class of the material under test, i.e. alteration of the material under test while maintaining the same basic structure such as, for example, a change of class of tobacco, class of coffee, class of milk product etc., has no effect for the purposes of the moisture content measurement, since the calibration curve is influenced only to an insignificant extent. Accordingly, a once plotted calibration curve can remain applicable also upon alteration of the class of material, as long as the basic structure of the material remains constant.

This is a consequence of the particular signal processing and of the microwave measurement technique, in which the influence—which is disturbing in the low-frequency range—of the ionic conductivity is of subsidiary importance. Upon a change of the material of different basic structure, the differing calibration curves can be stored and called up as required.

As a result of the matching selection of the frequency range of the measurement process as well as the particular matching of the applicator as measurement pick-up to the material under test, inhomogeneities within the range of the material covered do not have any disturbing effect.

The material moisture content is measured as the mean value, in contrast to measurement processes which possess only a small active measurement zone such as, for example, infrared processes or microwave processes using wavelengths below the size of the grain structures of the material under test.

Particular surface effects of the sample material have no effect in this measurement process. The microwave penetrates the sample in the active zone and is influenced in an evaluable manner by the material moisture content of the entire sample cross section concerned. This leads to the elimination of systematic measurement errors as occur, for example, in reflection measurement processes. In the case of measurement processes in which a microwave or infrared wave reflected at the sample surface is evaluated, considerable measurement errors arise as a result of an alteration of the roughness of the surface, of the color, or on account of systematic deviations of the surface moisture content from the material moisture content such as, for example, due to surface drying or due to concentration of moisture in the surface region in the case of pasty products when using pressing processes.

In physical terms, the measurement process is based on the evaluation of the dipol relaxation of the water molecules in a moist material sample. For this purpose, the material under test is brought into the electromagnetic field of the resonator in an optimal form matched to the material to be measured. With given geometric dimensions, the transmission of a resonator is decisively dependent upon the frequency: it shows resonance behaviour. If the material to be measured is situated in the electromagnetic field of the resonator, the resonance frequency of the resonator f(0) is reduced as compared with that of the empty resonator f(LO) while the resonance half-width value b(0) of the resonance line is increased as compared with that of the empty resonator b(LO). These two effects are the greater, the greater is the moisture content of the material. The resonance frequency reduction f(LO)−f(0) is a direct consequence of the wavelength shortening, especially due to the water in the sample; the line widening b(0)−b(LO) is a direct consequence of the conversion of electromagnetic energy into heat by the water component in the material under test. However, the two metrologically detectable parameters are affected not only by the material moisture content but also by the packing density of the sample material within the field region of the resonator. In the case of correct matching of the applicator to the sample material, it is always possible to detect the influences of material moisture content and material density separately. Accordingly, the process is outstandingly suitable for measuring two process variables independently of one another at the same time, namely the material moisture content independently of the packing density, if a moisture content calibration has been undertaken by means of reference measurements, the material density independently of the material moisture content, if a density calibration has been undertaken by means of reference measurements.

Figure 2:
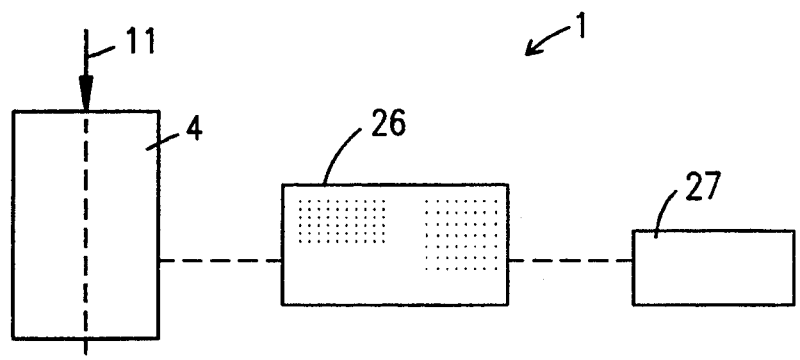
Figure 3:
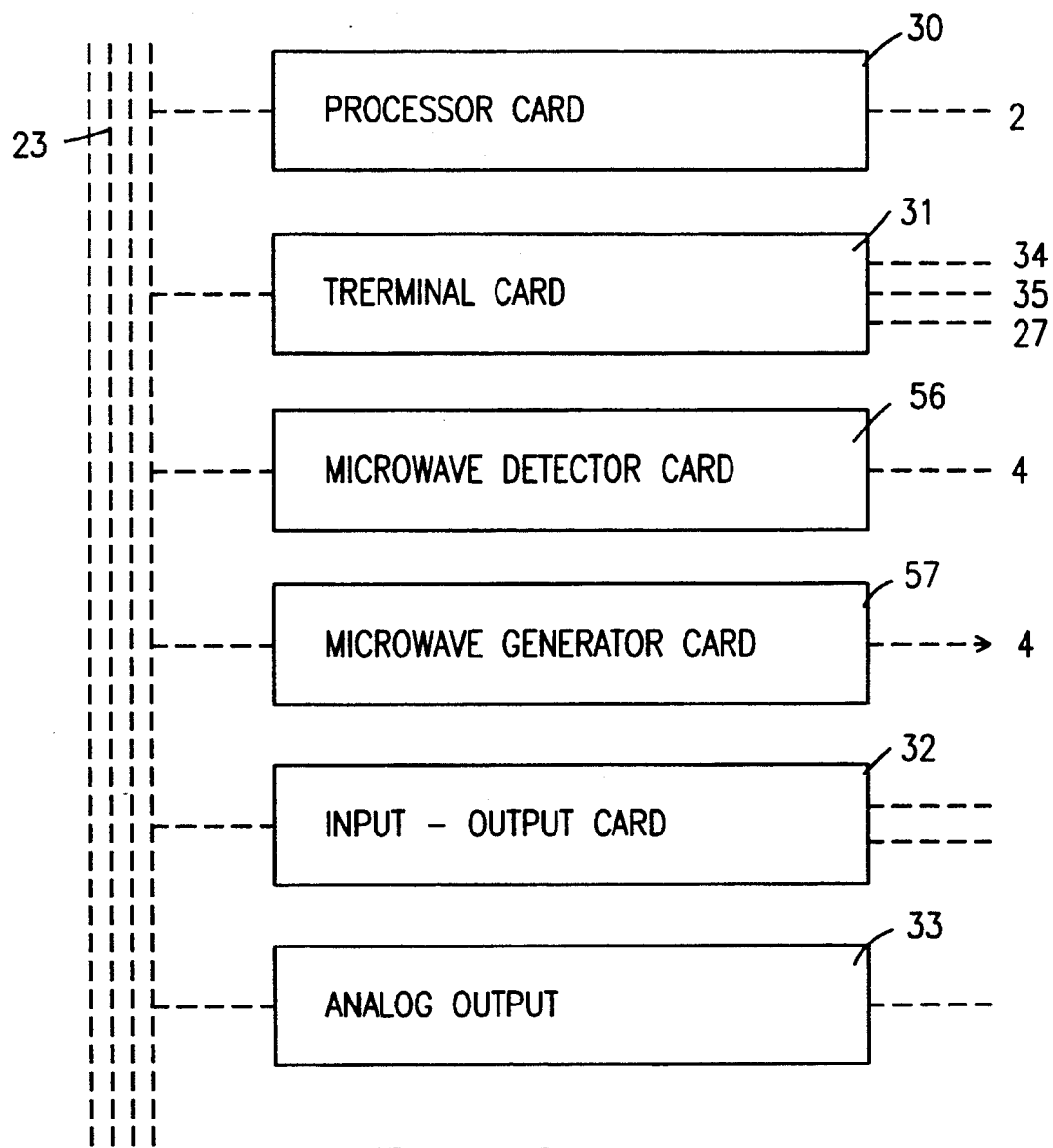
Figure 3A:
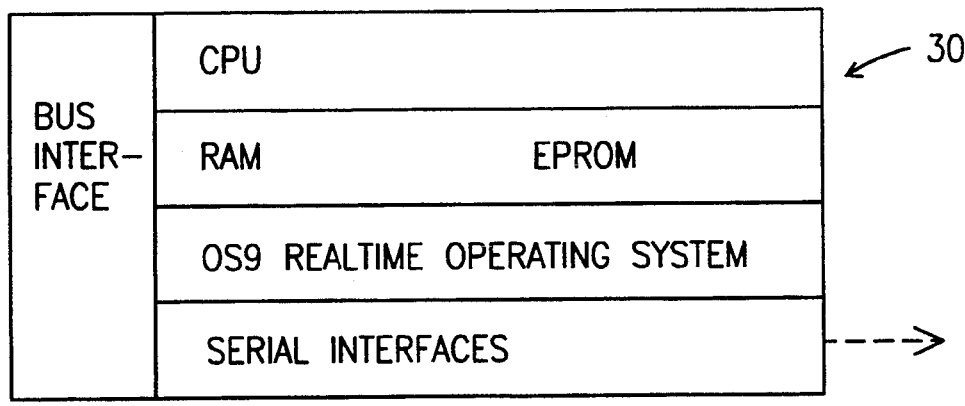
Figure 3B:
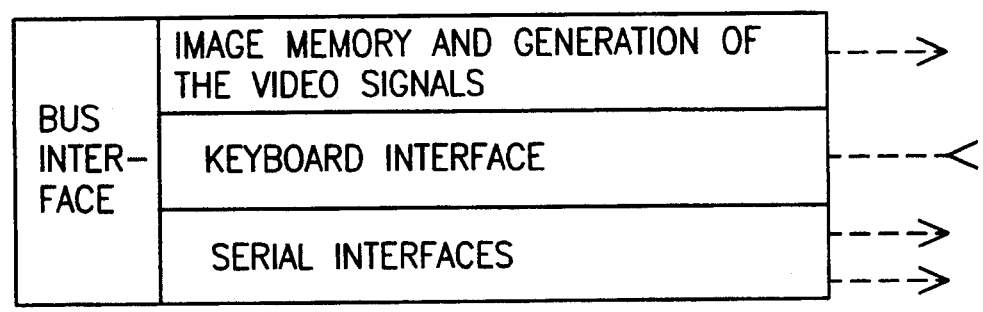
Figure 3C:
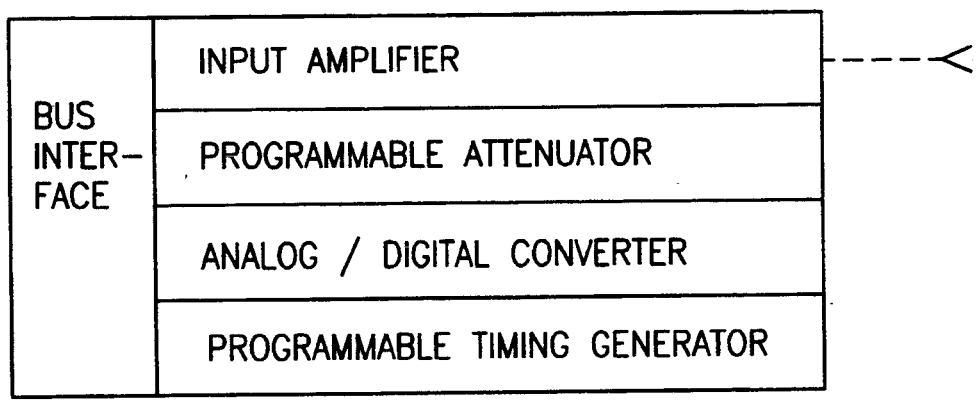
Figure 3D:
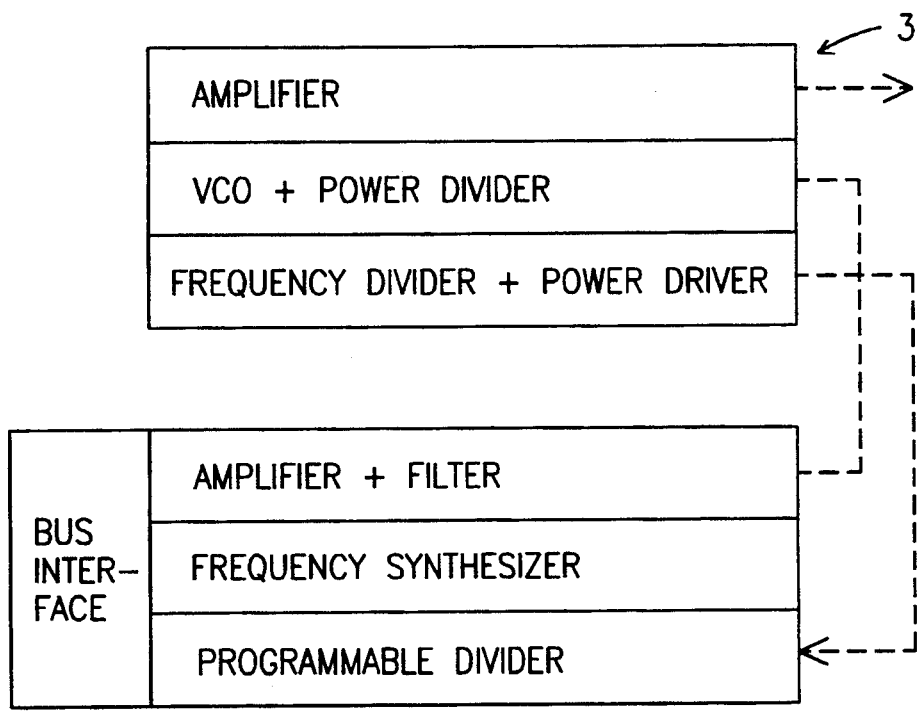
Figure 3E:
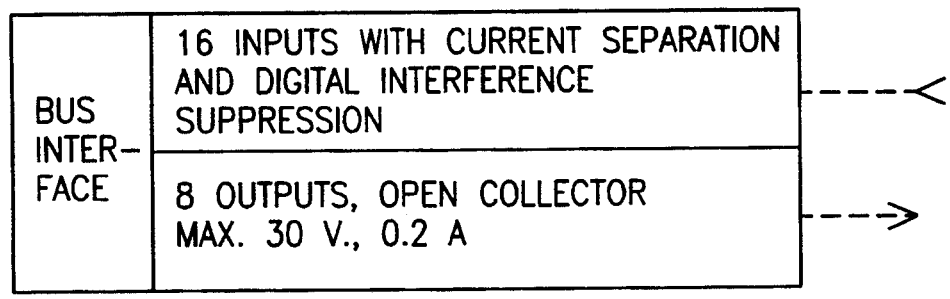
Figure 3F:
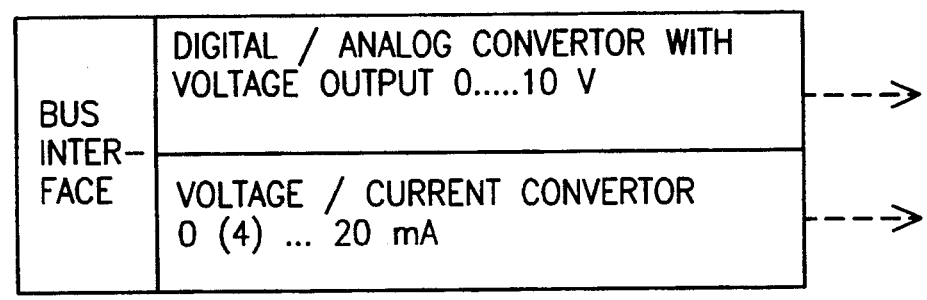
Figure 4:
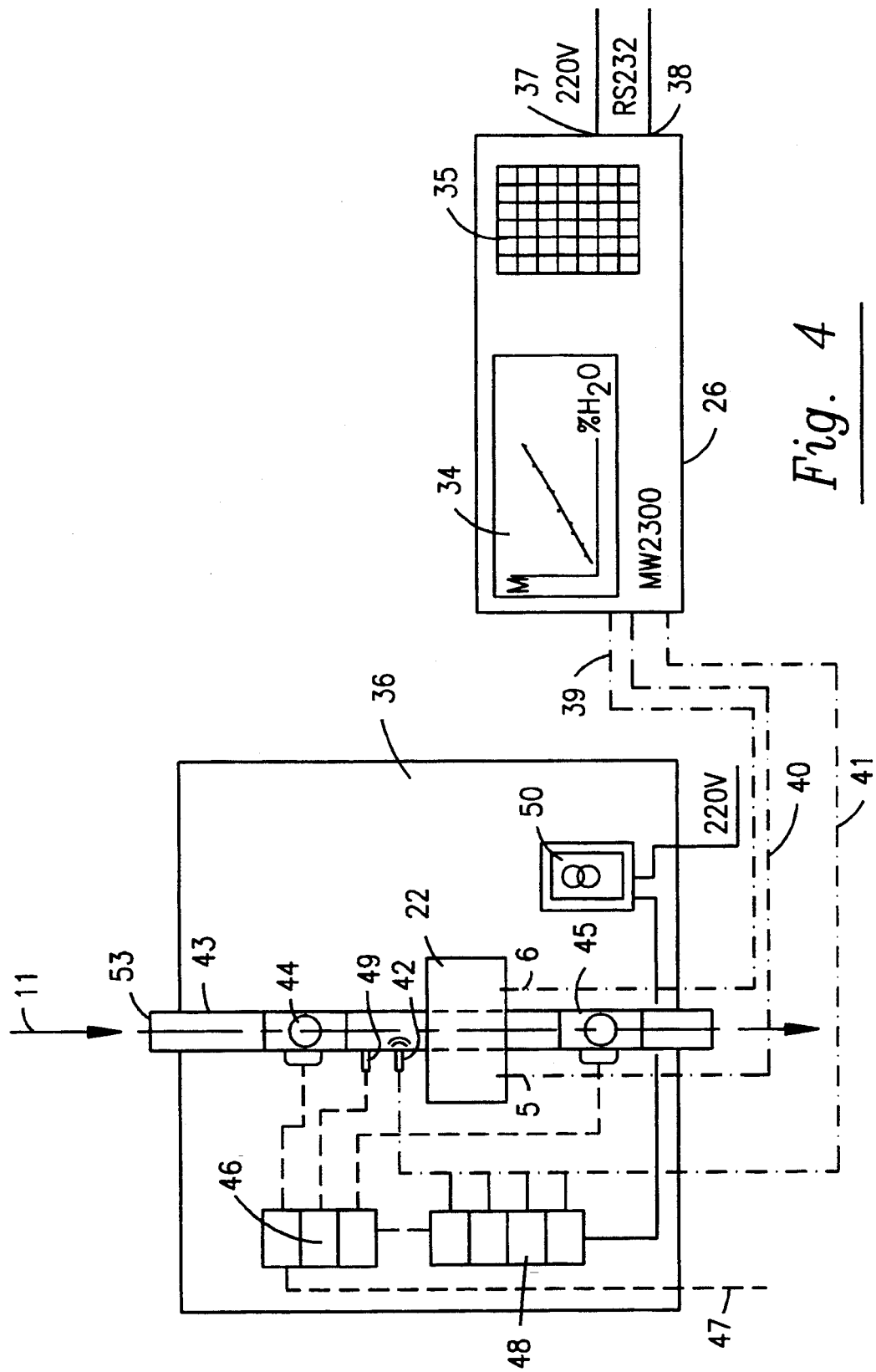
Figure 5C:
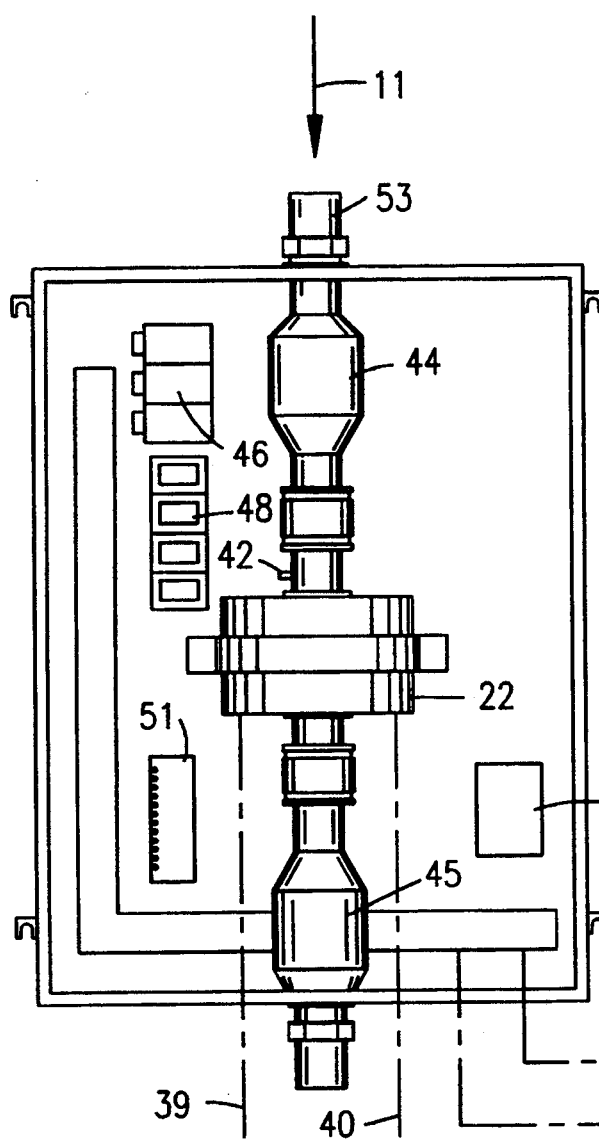
Figure 5C:
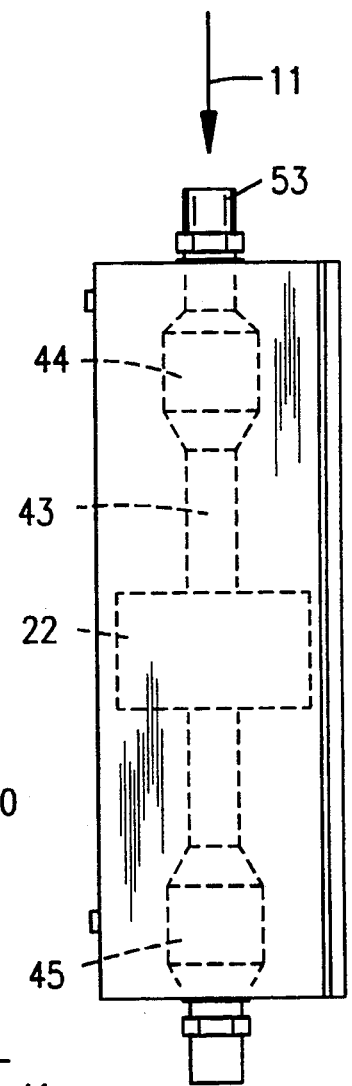
Figure 5C:
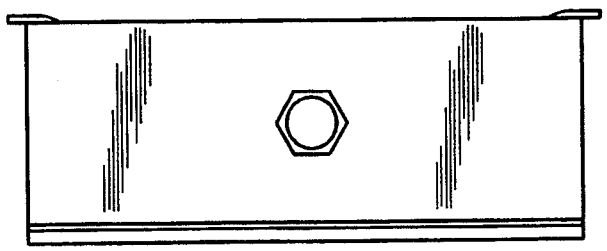
Figure 6:
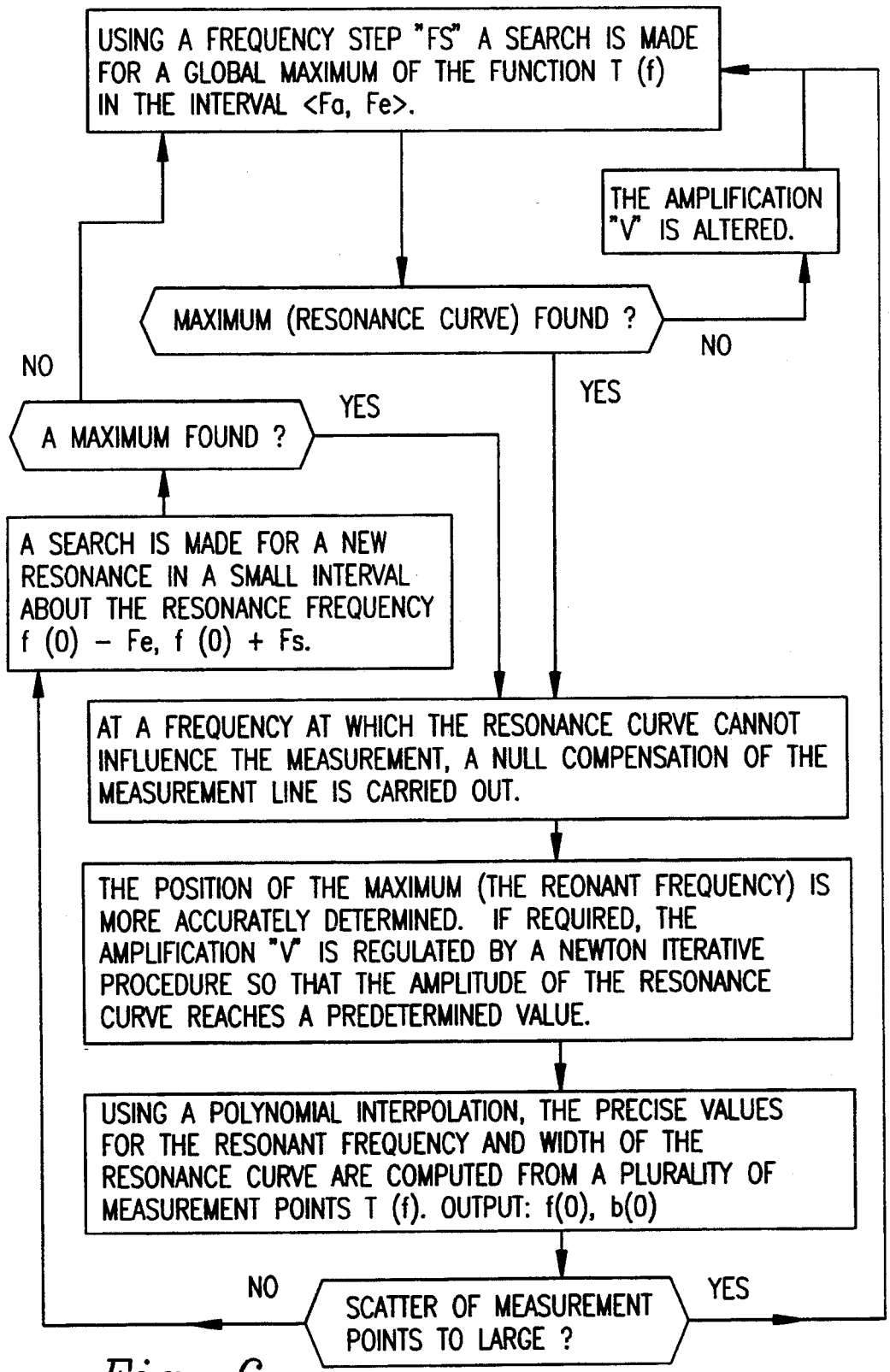
Figure 7B:
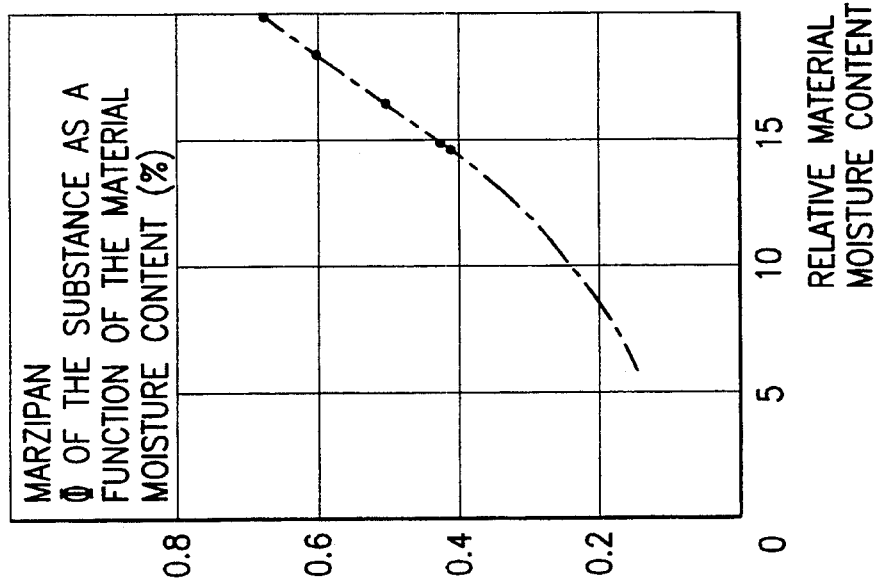
Figure 7A:
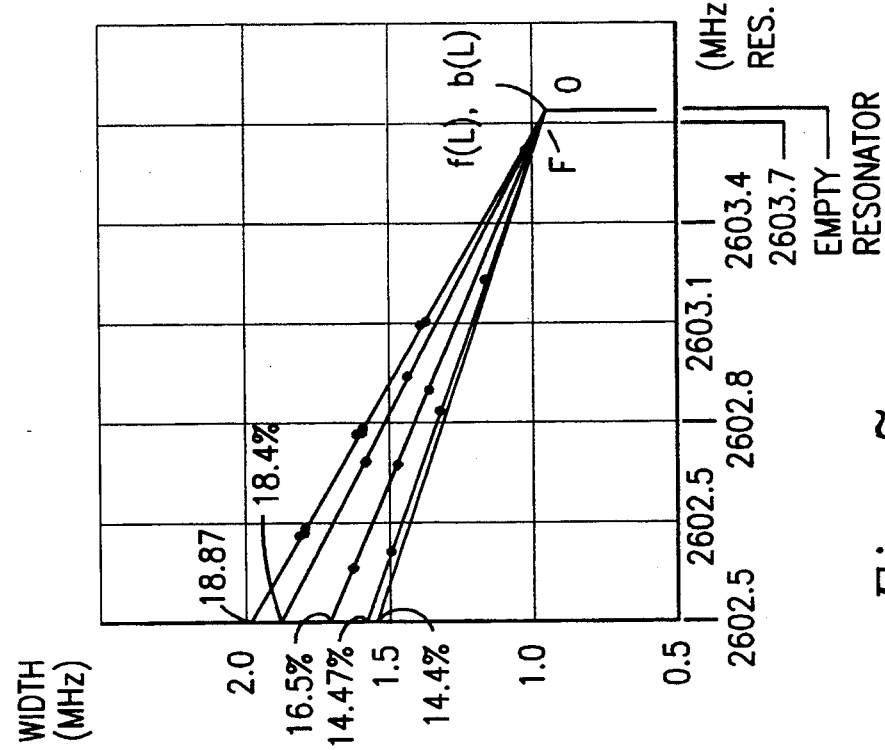
Figure 11A:
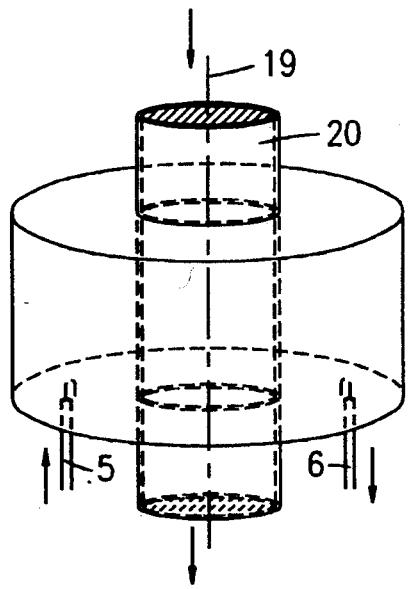
Figure 11B:
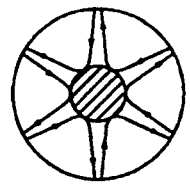
Figure 11C:
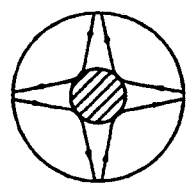
Figure 12:
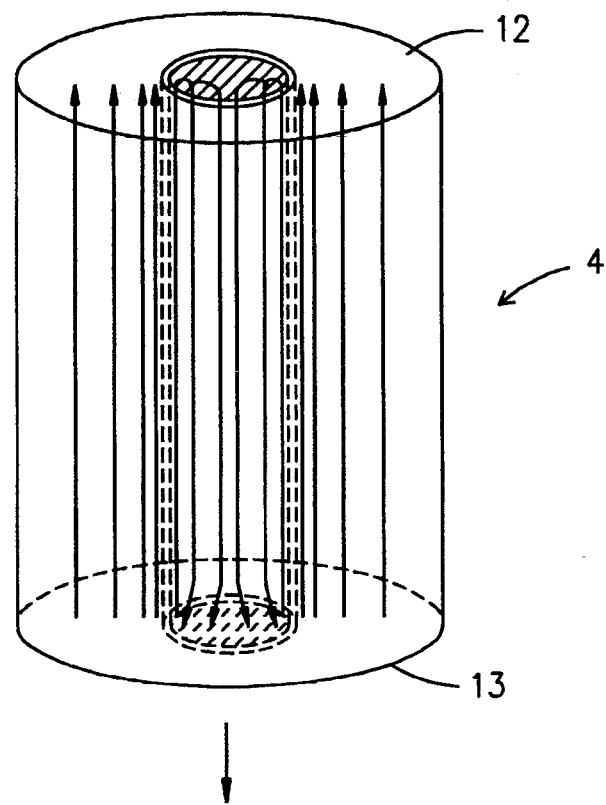
Figure 15A:
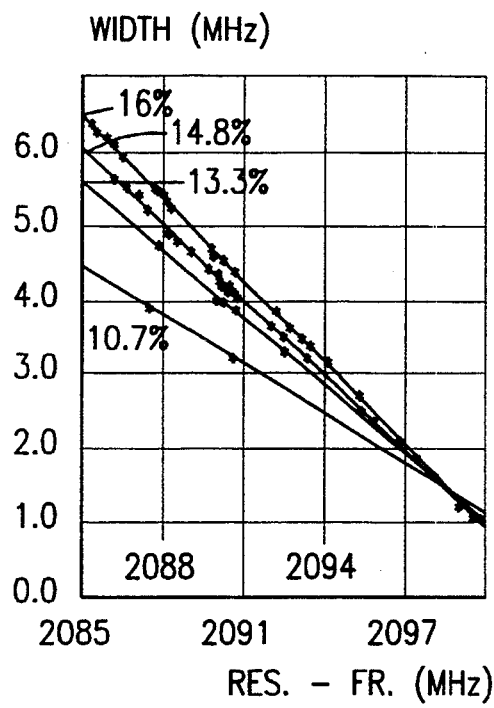
Figure 15B:
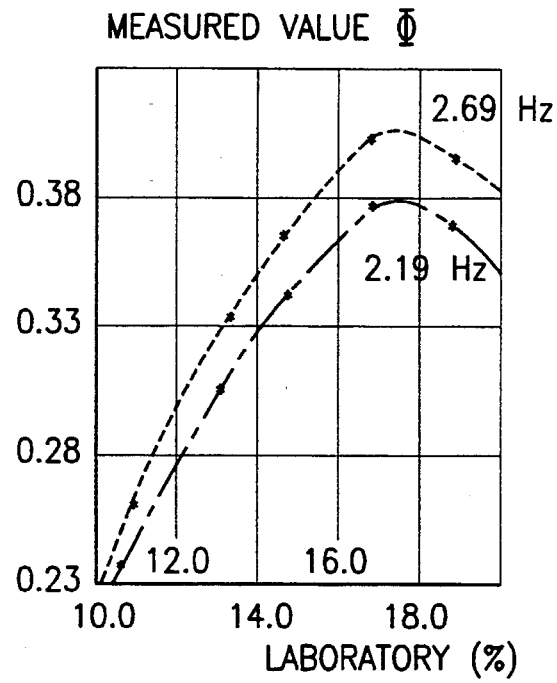
Figure 17:
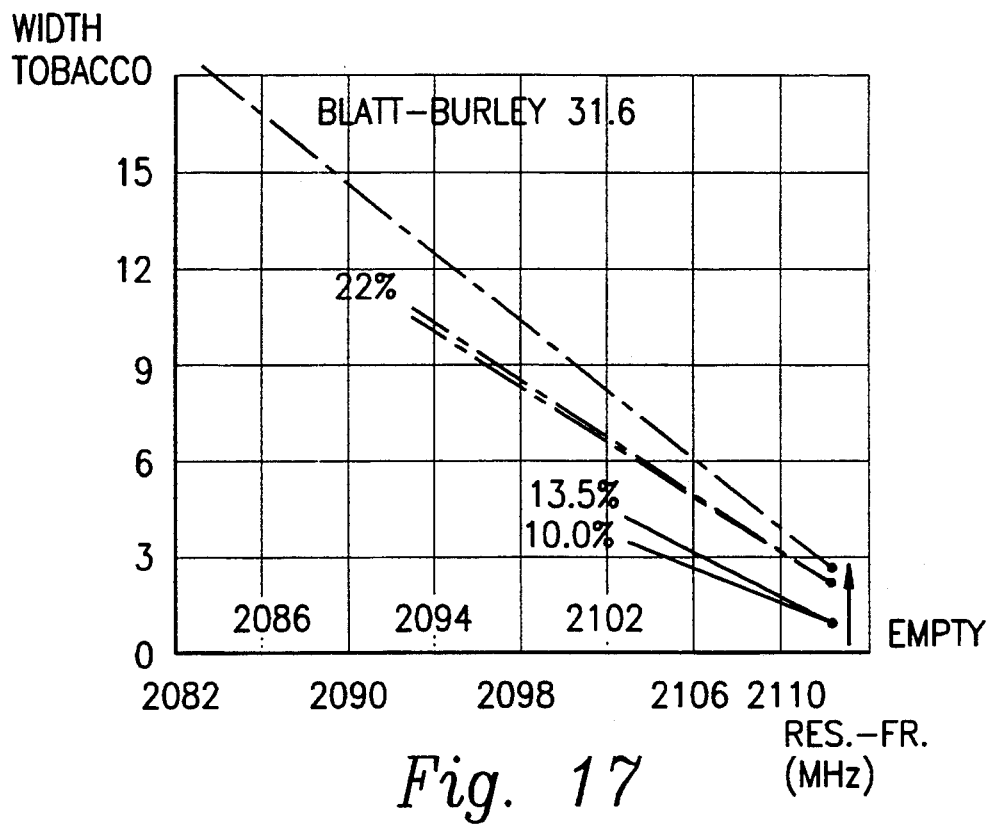
Figure 19:
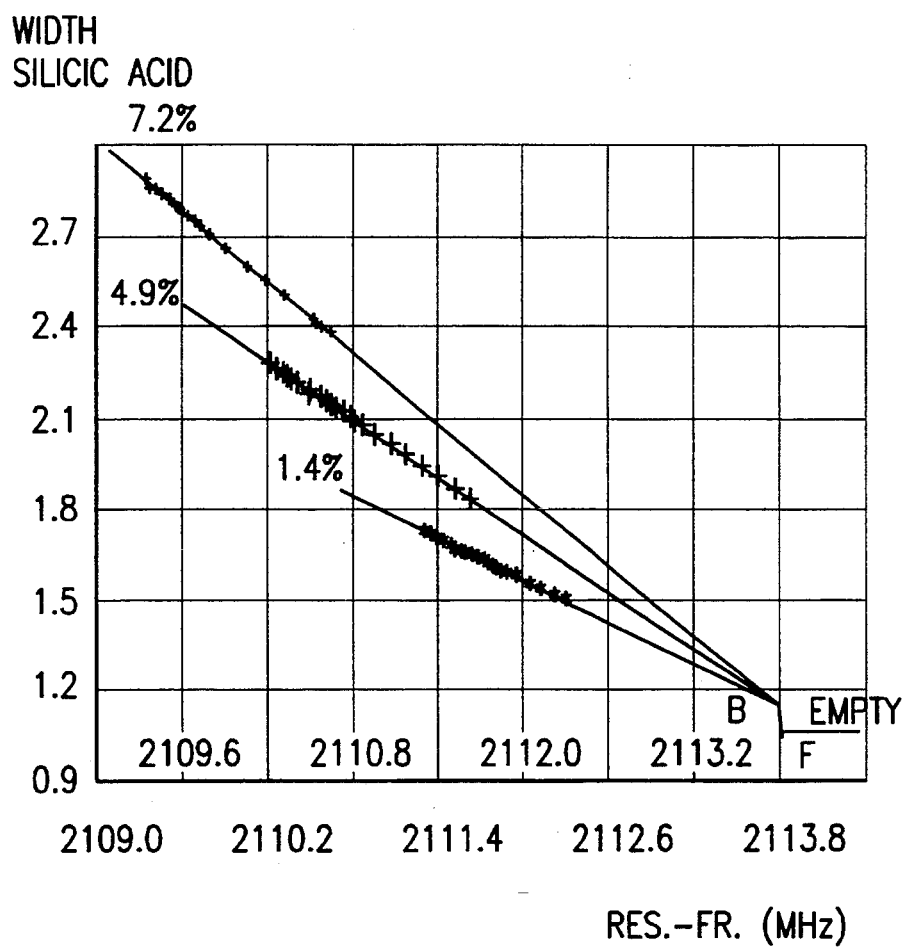

The invention is explained in greater detail hereinbelow with reference to the example of the device shown in the drawings. In the drawings:

FIG. 1 shows the device in a diagrammatic representation in the form of a circuit diagram, FIG. 2 shows the block diagram of the device according to FIG. 1, FIG. 3 shows the block diagram of the evaluation unit according to FIG. 2, FIGS. 3a show the components of the evaluation unit to 3f according to FIG. 3 in a diagrammatic representation, FIG. 4 shows the device according to FIG. 1 in a diagrammatic front elevation, FIGS. 5a show the measurement station with resonator of to 5c the device according to FIG. 1 in a diagrammatic side elevation, transverse elevation and plan view, FIG. 6 shows a flow diagram over the temporal sequence of the plotting of the resonance curve, FIGS. 7a show diagrams with examples of the moisture to 10b content measurement in a pasty product, in tobacco, in roast coffee and in a fine-grain pulverulent substance, FIG. 11a shows a diagrammatic representation of an applicator in a perspective view, FIGS. 11b show diagrammatic representations of the and 11c electric field lines of two probes in an applicator according to FIG. 11a, FIGS. 12 show further refinements of an applicator to 14 in diagrammatic perspective views, FIGS. 15 show two calibration curves for a substance and 16 measured at two resonant frequencies according to FIGS. 11b and 11c, a diagrammatic representation of the evaluation of a multi-valued calibration curve such as that in FIG. 15, FIGS. 17 show the density independence in the moisture to 18 content measurement of different products FIG. 19 shows the separation of the influence of moisture content and of density on the resonance signal.

FIG. 1 shows the basic structure of a device 1 for moisture content measurement. This device consists of an applicator 4 into which a sample 11 can be introduced. Two coupling probes 5, 6 associated with the resonator are arranged in the applicator 4. The coupling probe 5 is connected to a microwave generator 3. The coupling probe 6 is connected via a microwave amplifier or attenuator 7 to a detector diode 8, to which an analog/digital converter 9 is connected. This converter is connected to a processor 2, which is connected via a digital/analog converter 10 to the controllable microwave amplifier or attenuator 7. The desired frequency of the microwave generator 3 is controlled by the processor 2 via a further connection. Between the microwave generator 3 and the coupling probe 5 as well as between the coupling probe 6 and the microwave amplifier or attenuator 7 there is respectively disposed a circulator 28 for decoupling. Measured values of the temperature of the sample 11 are likewise fed to the processor 2. The microwave generator 3 is operated in a wide frequency range and exhibits a PLL circuit. The evaluation unit may be equipped, for example, with a 68020 microprocessor with multitasking and EPROM-capable OS-9 real-time operating system. It undertakes both the communication with the user, the data administration directed by the user and the execution of the measurement functions and also the further processing of the data for a process control. Using the quartz-stable microwave generator 3, which is digitally tunable by the processor 2, the microwave power of variable frequency is generated within the required frequency range. The frequency required in each instance by the processor 2 is set within a few milliseconds (VCO within the limits of a PLL control loop) and fed to the applicator 4, which contains the sample material to be measured. In this case, the applicator 4 accepts the material under test either in the form of a test sample or, in "on-line" operation, in the material flow.

The microwave signal emerging from the applicator 4 is fed via a settable integrated microwave amplifier or attenuator 7 to a Schottky barrier detector diode 8, the LF signal of which is evaluated by means of an analog/digital converter 9 by the processor 2.

The microwave amplifier or attenuator 7 is controlled by the processor 2 so that in the event of maximum transmittance of the applicator 4 designed as a resonator, when the microwave frequency coincides with the current resonant frequency of the resonator, the detector diode 8 always receives the same microwave power.

In this manner, the resonance line of the applicator 4 can be measured with an accuracy which is substantially enhanced as compared with conventional resonance measurement processes, i.e. the resonant frequency f(0) and the line width b(0) can so be determined. As a result of the processor control of the microwave generator 3, the desired microwave frequency can be set precisely in narrowly predetermined frequency steps by means of a PLL circuit. As a result of the processor control of the upstream microwave amplifier or attenuator 7, the detector diode 8 can always be operated at the same working point of maximum signal power, whereby the disturbing influence of nonlinearities of the diode is avoided. The diode signal of a microwave frequency can be detected far outside the resonance of the applicator 4 and can be utilized as null compensation both of the entire measurement line and also for the evaluation of the resonance line.

The accuracy of measurement achieved in this manner in the course of normal operation for the determination of the resonance frequency f(0) has displaced the relative measurement error below the value of $$\Delta f / f(0) < 3 \times 10^{-7}$$

FIG. 2 shows a schematic block diagram of the device 1 and illustrates that this device exhibits as the principal elements the applicator 4 for the sample 11 to be measured, an evaluation unit 26 and a printer 27 to output the measured values. FIG. 3 shows a block diagram of the evaluation unit 26 with a diagrammatic representation of its components. A processor card 30, a terminal card 31, the microwave amplifier or attenuator 7, the microwave generator 3, an input-output card 32 and an analog output 33 are connected to a bus 29. The processor card 30 is connected to the computer 2. To the terminal card 31 there are connected a display 34 for the conduct of dialog and observation of the measurement, a keyboard 35 and the printer 27. The microwave detector card 56 includes the microwave amplifier or attenuator 7, the detector diode 8, the analog/digital converter 9 and the digital/analog converter 10. The microwave generator card 57 exhibits the microwave generator 3, the output signal of which is conducted to the applicator 4. The input-output card 32 serves for the control of the applicator 4. A remote display for the process regulation can be connected to the analog output 33. A digital interface permits the connection of the measuring system to a process management computer.

FIGS. 3a to 3f show the essential components contained in the processor card 30, the terminal card 31, the applicator 4, the microwave amplifier or attenuator 7, the microwave generator 3, the input-output card 32 and the analog output 33.

FIG. 4 shows the device 1 in a diagrammatic side elevation. The evaluation unit 26 with display 34 and keyboard 35 exhibits a grid connection 37 and an interface 38 to which, for example, the printer 27 can be connected. By means of measurement lines 39, 40 and a control line 41, the evaluation unit 26 is connected to the coupling probes 5, 6 and a level probe 42, which are disposed in the resonator 22 or in the direction of material flow in front of the latter in the sample tube 43. The resonator 22 and the sample tube 43 are situated in a measurement station 36. In the direction of material flow in front of and behind the resonator 22 there is provided a respective shut-off component 44, 45. The shut-off components 44, 45 are acted upon with compressed air via magnetic valves 46, which are connected to a compressed air line 47. The magnetic valves 46 are controlled by relays 48. The relays 48 are connected to the control line 41 and are connected to a voltage supply 50. Furthermore, a flushing air connection 49 is provided in the sample tube 43, which connection is likewise connected to the magnetic valves 46. FIGS. 5a to 5c show the measurement station 36 in different views. The relay 48 is connected via terminals 51 to the voltage supply 50. The material feed 53 is disposed at the upper portion of the measurement station housing 52 and serves for the filling of material under test. A compressed air connection 54 for the compressed air line 47 is provided on the floor of the measurement station housing 52. The product is returned into the main product stream via a second shut-off component 45.

FIG. 6 shows, in a flow diagram, the temporal sequence of the various computer steps in the control of the process of the plotting of the resonance curve. They proceed from the search for the current resonance maximum via the null compensation far outside the resonance, to the establishment of the required microwave amplification or attenuation for the purpose of bringing the maximum value of the resonance curve to a preselected value, further to the plotting of the exact measurement points of the resonance curve, to the arithmetic polynomial interpolation of the resonance line measured values, for the precise determination of the resonance frequency f(0) and resonance half-width value b(0).

As has already been mentioned, the two process variables f(0) and b(0) are dependent both upon the material moisture content and also upon the material density. However, it is possible to separate the influence of the two variables. Subject to the condition that the correctly matched type of resonator is employed for the measurement function, the influence of material moisture content and material density can be separated for any dielectric substances, extending into the range of very high dielectric constants and thus also high material moisture contents.

If $\rho$ designates the density of the material which is situated in the resonator field and $\Psi_r$ represents the relative material moisture content, then measurement shows that the width alteration b(0)-b(L) and the frequency alteration f(0)-f(L) of the resonance line exhibit the same dependence upon the density of the material as compared with the reference quantities b(L) and f(L) to be determined experimentally, irrespective of the material moisture content. This common density function X($\rho$) increases with increasing density monotonically and in general as a nonlinear function of $\rho$.

It is essential that it is experimentally possible to determine the reference quantities b(L) and f(L) so that a single function X($\rho$) can be stated, which describes in the same manner the density dependence of b(0)-b(L) and f(0)-f(L). On this basis, the following product statement is applicable to the relation between the direct process variables b(0) and f(0) and the substance variables moisture content $\Psi_r$ and density $\rho$ to be measured; in this case, the empirical reference quantities for the line width b(L) and the resonant frequency f(L) are characteristic of a type of resonator as well as the class of material to be measured.

$$b(O) - b(L) = Y_b(\Psi_r) \cdot x(\rho) \tag{1}$$

$$f(L) - f(O) = Y_f(\Psi_r) \cdot x(\rho) \tag{2}$$

If the density-dependent factor X($\rho$) of the product statement is eliminated by division, then this gives a quantity Φ, which is entirely independent of the density ρ of the material and is dependent only upon the moisture content $\Psi_r$.

$$\Phi(\Psi_r) = \frac{b(O) - b(L)}{f(L) - f(O)} \cdot \frac{Yb(\Psi_r)}{Yf(\Psi_r)} \quad (3)$$

This quantity Φ, which is obtained from the primary process variables b(0), f(0) and the constant reference quantities b(L), f(L) is the actual measurement signal of the device 1 for moisture content measurement. It is dependent only upon the material moisture content. If it is present in stored form in the device 1 as a calibration curve, the material moisture content $\Psi_r$ can be displayed after the determination of Φ.

If the measured line width b(0) of the resonance line is plotted as a function of the resonance frequency f(0) at constant material moisture content and variable density, then the influence of the density fluctuation is revealed as follows. The measured values of the line width b(0) and resonance frequency f(0) alter so that the measurement points b(0) against f(0) lie on a straight line which passes through the point having the empirical parameters f(L), b(L) and the gradient of which is dependent only upon the moisture content of the material. According to equation (3), the following straight line equation is applicable:

$$b(O) = \frac{Yb(\Psi_r)}{Yf(\Psi_r)} \cdot (f(L) - f(O)) + b(L) \quad (4)$$

Accordingly, the significance of the empirical parameters b(L) and f(L) also becomes clear. In the resonance frequency/width plot, they represent the common point of intersection of all straight lines which arise by density variation and which are distinguished from one another in the material moisture content, i.e. in the straight line gradient, as is represented, for example, in FIG. 7a.

These two parameters b(L) and f(L), which are to be determined empirically, are defined for the use of a specified type of resonator, which is optimally matched for the process moisture content measurement problem to be handled, by a characteristic relation and are defined for the applicator 4 in the software of the computer 2.

These parameters are interrelated with the characteristic quantities of the microwave resonance line of the resonator without material under test, the empty line width b(LO) and the empty resonance frequency f(LO), via the following equations:

$$b(L) = b(LO) + B \quad (5)$$

$$f(L) = f(LO) + F \quad (6)$$

The two correction quantities B and F for the deviation of the density line intersection in the case of variable material moisture content from the empty resonator point are dependent both upon type of resonator and also upon the matching of the resonator to the material to be measured.

In particular, B and F do not alter if in consequence of alterations to the applicator 4 in the course of the measurements the empty resonator data b(LO) and f(LO) locally alter, for example as a result of contaminations of the applicator or as a result of thermal expansion upon alteration of the operating temperature.

On this basis, according to the equations (5) and (6) it is possible to compensate the influence of contaminations of the applicator 4 or of other alterations by simply measuring the resonance data of the empty resonator b(LO) and f(LO) in the normal long-term operation of the device 1. Using the equations (5) and (6), the new reference quantities b(L) and f(L) are computed and the measurement signal is determined, in accordance with equation (3), from the direct process variables b(0), f(0). In spite of contamination, it is then possible to undertake further processing with the same high measurement accuracy of the device, using the old calibration curve.

In the event of cleaning of the applicator 4, a corresponding procedure can be adopted. The device 1 for moisture content measurement can be used again immediately by simple measurement of the empty resonator data, without any requirement for a new calibration.

FIGS. 7a and 7b show, with reference to the example of a resonator matched for moisture content measurement in marzipan, the behavior described by equation (4) in the case of variation of the packing density of marzipan. It can clearly be seen that the line width and resonant frequency move along a straight line, the gradient of which is determined only by the material moisture content. The point of intersection, which is characterized by the correction quantities B, F, deviates considerably from the empty resonator point. This gives the calibration curve which, in FIGS. 7a and 7b, is typical of the moisture content measurement in marzipan, where the process variable Φ defined in accordance with equation (3) is plotted against the reference moisture content (drying cabinet method).

Figure 8A:
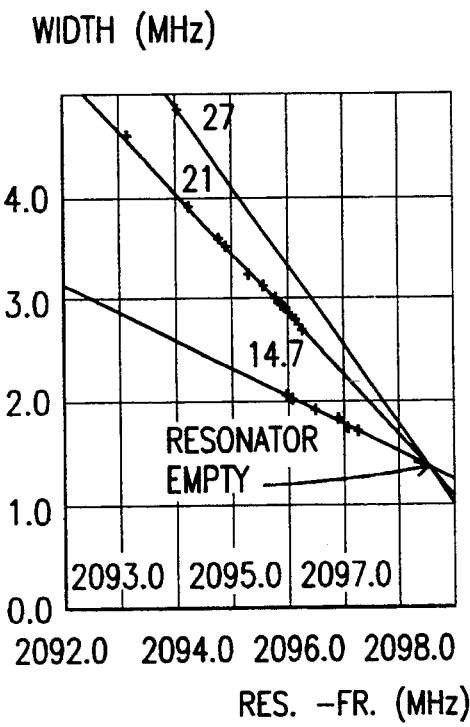
Figure 8B:
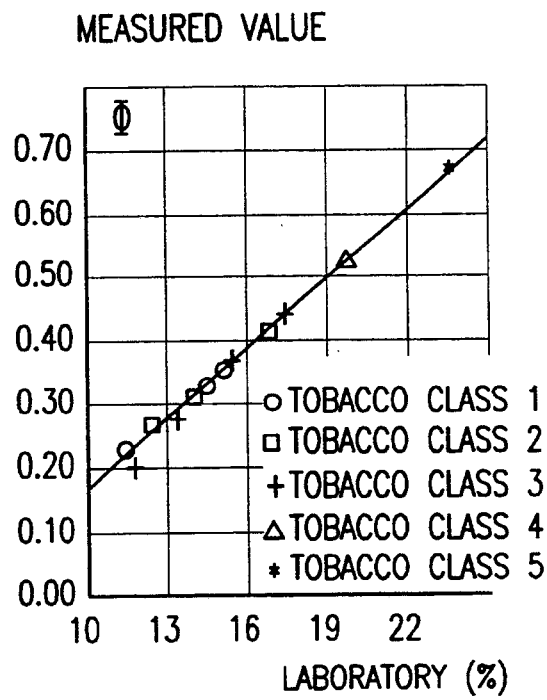

FIGS. 8a and 8b show the corresponding measurement results on tobacco in the range between 11 and 25 percent material moisture content; the comparative measurements for the calibration of the system were also in this instance carried out using a drying cabinet.

In the case of this application, the particular feature emerges that the correction quantities B, F in equation (4) and (5) become almost zero, i.e. the empty resonator data themselves in equation (3) form the reference quantities. Furthermore, it is seen that the calibration curve of the process variable Φ alters only slightly in the event of a change of the classes of tobacco with differing growing area and differing pretreatment.

Figure 9A:
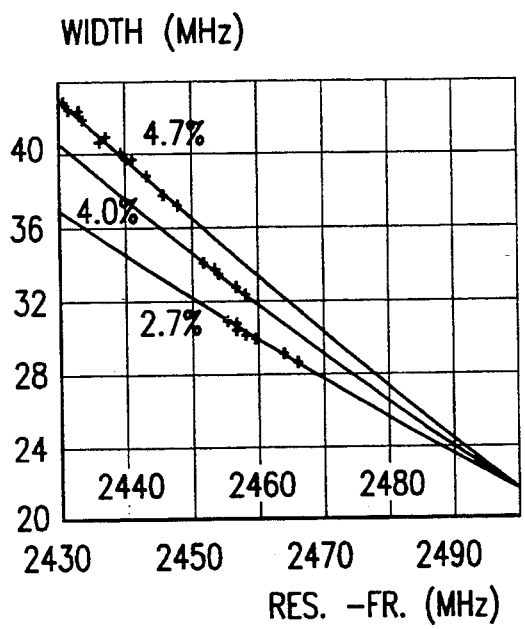
Figure 9B:
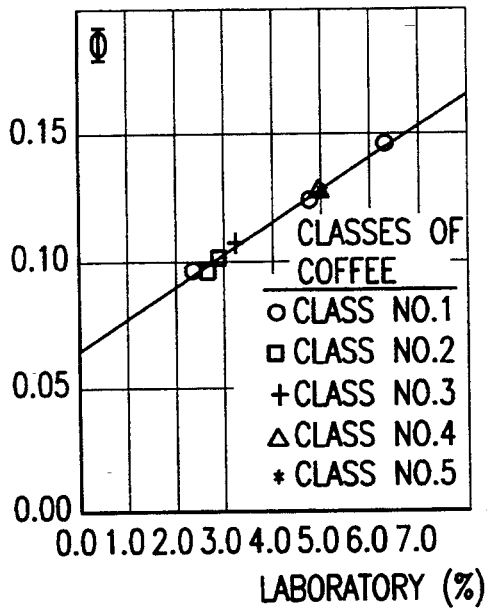

This class independence of the measurement signal becomes even clearer in the calibration curve comparison, shown in FIGS. 9a and 9b, of roast coffee beans of the most widely varying roasting processes: Irrespective of the growing area and roasting process, the same calibration curve is applicable for the moisture content measurement.

The causes of this class independence of the measurement process are the reduction of the influence of ion conductivity effects due to the use of the microwave measuring technique and the particular type of signal processing carried out in accordance with equation (3). Class influences which are still present act on resonant frequency shift and line broadening similarly to the material density alteration in the same way and are removed in the course of division in equation (3) in order to obtain the measurement signal.

Figure 10A:
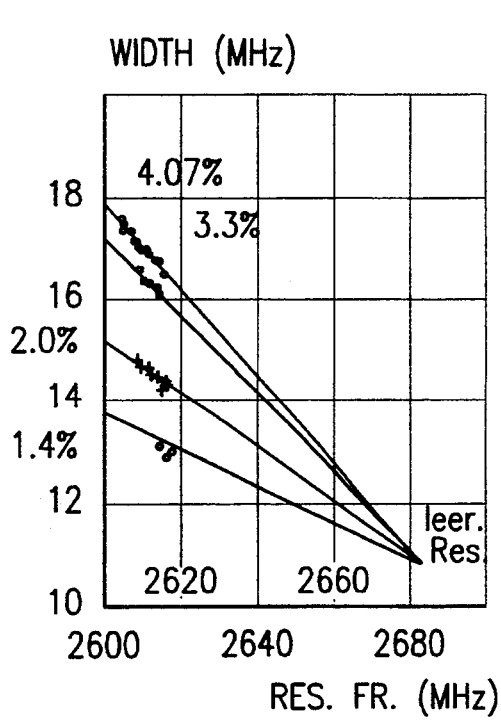
Figure 10B:
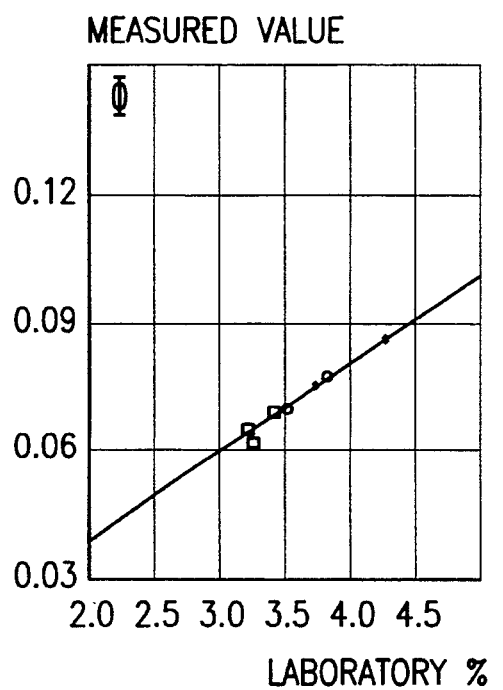

FIGS. 10a and 10b show, with reference to moisture content measurements in cocoa powder intended for automatic machines, that even in the case of a marked variation of additives in the material under test, such as in this case of sugar, the calibration curve of the measurement signal does not alter, i.e. now, just as previously, it is possible to operate using a single calibration curve.

The plotting of a calibration curve can be undertaken in a simple manner by the operator of the device 1 under operational conditions, as soon as he is able to determine the reference moisture content for the calibration by a reference measurement (e.g. by using the drying cabinet method). A separate second measurement with samples of defined form and composition is dispensed with, as is the necessity to measure the microwave properties of the dried sample material, as is necessary in other known microwave processes.

In order that the laws described in equations (1) (6) should be applicable, the applicator must be matched to the respective moisture content measurement function. In this connection, it is necessary to observe the following:

The coupling of the sample 11 to be measured to the resonator of the applicator 4 has to take place so that its resonance behaviour is disturbed only slightly.

Deelectrification effects, and thus a more or less complete reduction of the moisture content sensitivity of the process variable $\Phi$ defined in equation (3) may be avoided by ensuring that the electric field of the resonator extends parallel to the surface in the course of the transition into the material of the sample 11. The electric field must not enter into the sample 11 perpendicular to the surface of the material to be measured.

These conditions may be satisfied by the particular design of the type of resonator for matching to the measurement function.

A solution which is satisfactory for many practical applications for material moisture content measurement is achieved if a circular-cylindrical type of resonator is designed so that within the frequency range entering into consideration the H311 and H211 resonances can be employed. For this purpose, the resonator must be provided with an opening and an internal cladding for sample introduction, in the central region in which the electric field strength becomes minimal. Such an applicator 4 is shown in FIG. 11a. A tube 20 is guided through the resonator, coaxially with the longitudinal axis 19. Between the tube 20 consisting of dielectric material and the resonator casing 21 there are disposed, opposite one another, the coupling probes 5, 6.

Using such an applicator 4 it is possible, in particular, to measure bulk materials in the "on-line" process or using sample removal. Pasty products or materials which require a container can, for example, be introduced into the resonator in a cup-shaped sample holder. A particular requirement on the form of the sample need not be imposed. The maximum possible diameter of the tube 20 is limited by the requirement that no electromagnetic emissions are generated as a consequence of the wavelength shortening in the sample material.

As shown in FIGS. 11b and 11c, two resonance lines can simultaneously be measured within the measurable frequency range on the same product, which resonance lines differ from one another in their resonant frequency by approximately 25 percent. These are the $H_{311}$ resonance with hexagonal field symmetry and the $H_{211}$ resonance with square field symmetry, both of which satisfy the initially mentioned conditions in that the sample 11 to be measured is disposed in the edge region of the electric field of the resonator, i.e. at its center.

The measurement results which are shown in FIGS. 8a and 8b for tobacco and in FIGS. 9a and 9b for roast coffee by way of example were obtained using an applicator according to FIG. 11a.

Furthermore, a particular design of the circularcylindrical resonator, which design exhibits the E010 resonance in the available frequency range, i.e. the fundamental resonance of the circular-cylindrical resonator, can be used for the moisture content measurement technique in particular practical applications, with advantage.

Especially when using materials having a low dielectric constant, and which have an elongate form (e.g. on a cigarette web, woolen thread, etc.) or which can be brought into an elongate form (e.g. fine-grain bulk material) use can be made of the fact that the electric field runs parallel to the sample surface. For these applications, the cylindrical applicator 4 shown in FIG. 12 is particularly suitable. The sample tube consists of dielectric material. The sample 11 is fed through an opening in the one end surface 12 and emerges from the other end surface 13. In this case, the E010 resonance of a circular-cylindrical resonator is used for the moisture content measurement.

The measurement points shown in FIGS. 10a and 10b for cocoa powder were obtained using an applicator 4 according to FIG. 12.

In the case of measurement functions where the dielectric constant of the material or the material moisture content are greater (e.g. moisture content measurement in marzipan, pasty products etc.), this type of resonator can be used if the sample 11 is rolled out or coated thinly on a dielectric substrate. In these circumstances, the electric field is scarcely attenuated upon entry into the surface of the sample. The measurement points shown in FIGS. 7a and 7b for marzipan were obtained in this manner.

Figure 13:
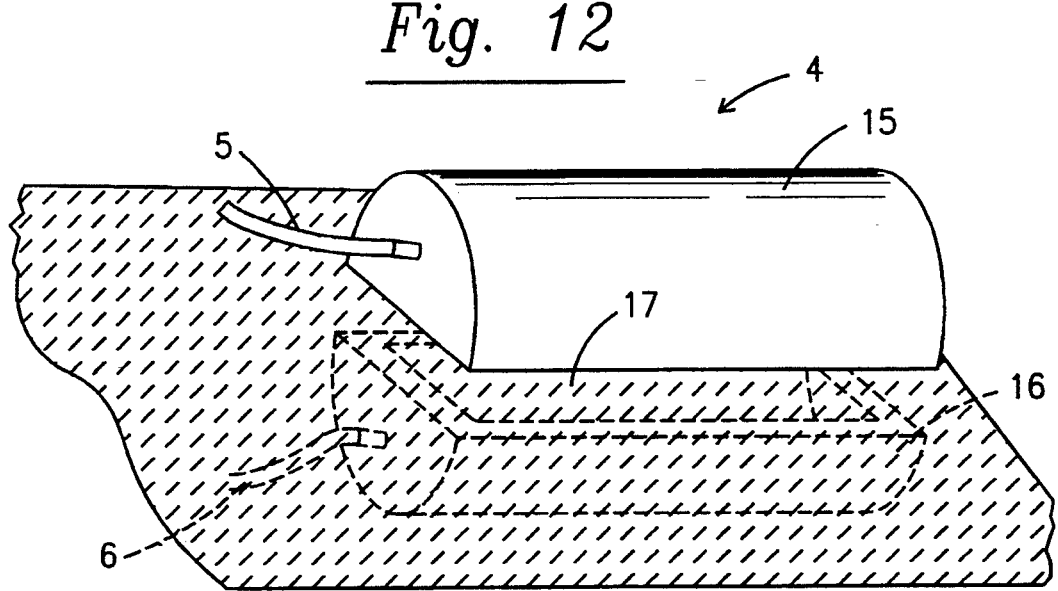

As far as moisture content measurement in foils, paper webs or textile webs etc. is concerned, particular suitability is exhibited by a circular-cylindrical or rectangular design of an applicator 4, which can be excited in the E010 resonance. For this purpose, as in FIG. 13, the resonator is cut open in the direction of the wall currents, provided with a dielectric internal cladding and mechanically secured so that the material web 14 is conducted in the direction of the electric field through the slit 17 of the resonator 4. Microwave detector and generator can be connected either, as illustrated, by the different resonator halves, or by one and the same resonator half.

Figure 14:
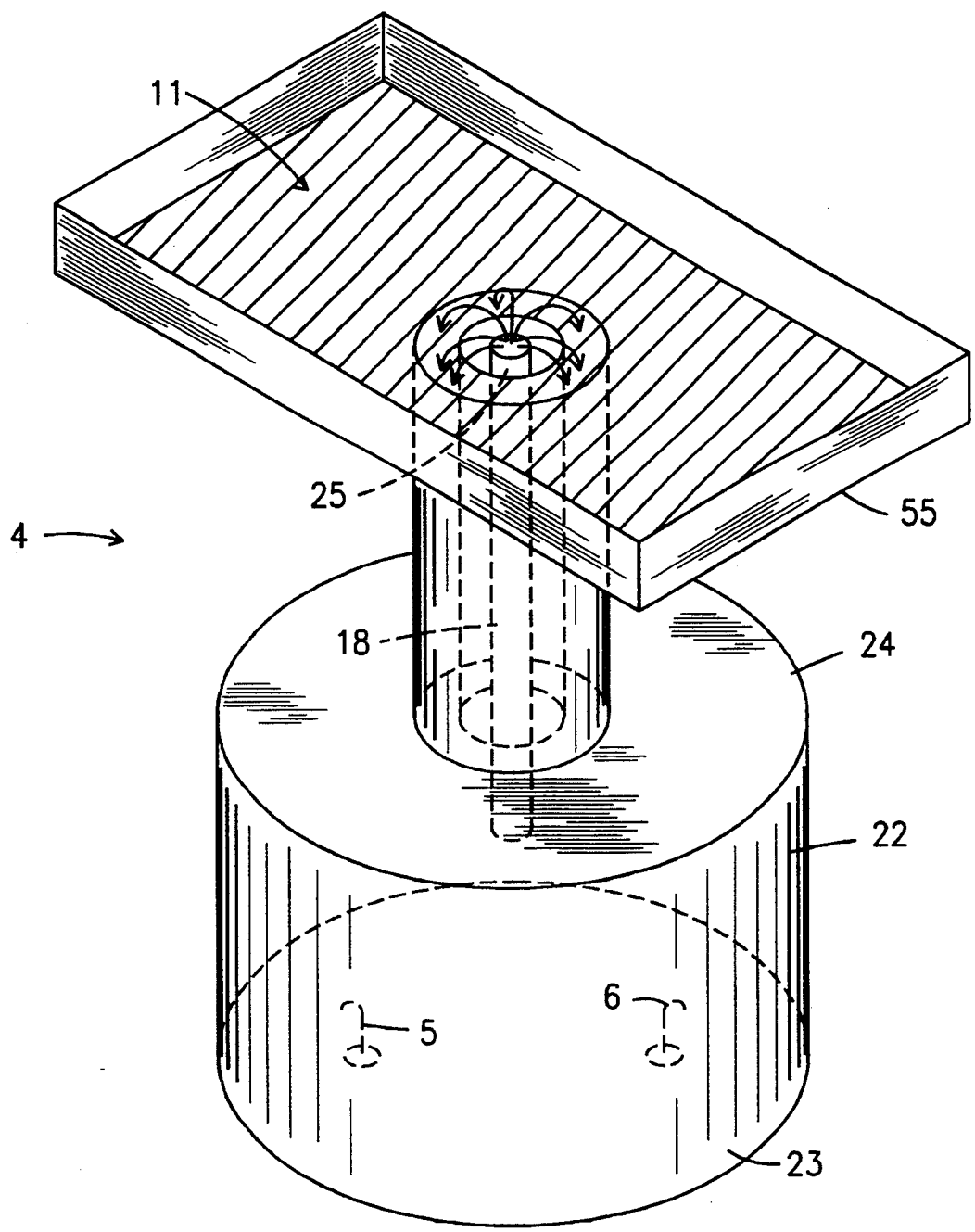

A further applicator 4 which is suitable for numerous practical applications for moisture content measurement especially in pasty products is shown in FIG. 14. In this case also, the law forming the basis of equation (3) can be applied in the event of the observance of defined conditions. The cylindrical closed resonator 22 is again operated in the E010 mode.

The coupling probes 5, 6 are passed through the lower end surface 23. By means of a coaxial line 18 passed through the upper end surface 24, and having the length of one quarter wavelength, a small proportion of the microwave in the resonator 22 is coupled out. At the free end portion 25 of the coaxial line 18, the stray field of the electromagnetic wave penetrates into the sample 11, which is situated on a sample carrier 55. The condition of the parallel penetration of the electric field strength into the sample surface can be satisfied by the selection of the appropriate spacing of the sample from the opening of the coaxial resonator. In order to measure $\Phi$, the interaction of the moist material of the sample 11 with the electric stray field at the open end of the coaxial line 18 is utilized.

In spite of the relatively small sample region covered by the electric field, the advantage of this measurement method is that the sample material does not need to be passed through the resonator. Rather, the material can be conducted away over the active zone of the applicator 4, if the applicator 4 is flanged on or screwed into material guides, bearing plates, pipes, etc.

The described types of applicators 4 show that the density-independent and class-independent microwave measurement process based on equation (3) can be used for the material moisture content by the appropriate selection of the applicator 4 for a multiplicity of set tasks arising in practice.

The metrological evaluation of the measurement signal $\Phi$ obtained in accordance with equation (3) presents, in a few practical applications, the problem that with increasing material moisture content the quantity $\Phi$ does not continuously increase as in FIGS. 7a to 10b, but, after exceeding a maximum, decreases again. If this maximum does however fall within a moisture content range which is of interest to the user, the result in the case of the evaluation of $\Phi$ would be possible ambiguities in the association of $\Phi$ and the material moisture content $\Psi_r$.

FIG. 15 demonstrates this with reference to the example of parmesan cheese, where, at a moisture content of approximately 17%, the calibration curve has its maximum, whereas the moisture content range of interest for the purposes of the production process is between 8 and 25%.

As a result of the possibility of being able to measure the resonance behavior at the same time at two and more frequencies, the device 1 can be successful while entirely retaining all advantages of solving the problem of ambiguity, since the two calibration curves at the two frequencies differ from one another (FIG. 15).

Figure 16:
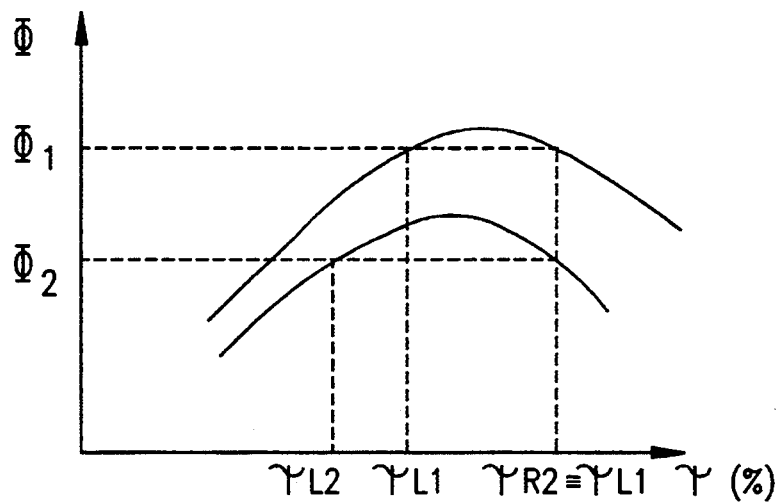

A possibility for overcoming the ambiguity is shown in FIG. 16. According to this, the two measurement signals $\Phi_1$, $\Phi_2$ are converted into a moisture content value at both frequencies using the respectively applicable calibration curve to the left and right of the maximum. The correct moisture content is then obtained as the mean value of the two moisture content values, the difference of which is a minimal.

The process variable $\Phi$ as a moisture-content-independent quantity can also be measured without knowing the properties of the empty resonator. This takes place in that the values of the half-maximum width and resonant frequency are measured in various density conditions of a sample in the resonator, these values are stored, the regression line is arithmetically determined, the value of the gradient of the straight line of the moisture-content-dependent measurement value is established and the moisture content value is determined via the calibration curve.

The process sequence when using this second mode of operation is as follows:

A calibration curve for the class of material to be measured is stored in the computer. After this, a sample with the same moisture content but different density conditions is brought into connection with the resonator so that the electric field of the resonator extends generally parallel to the surface upon the transition into the material of the samples. For each density condition of the sample, thereafter the halfmaximum width and resonant frequency are measured and stored. The regression line and thus its gradient are determined as measurement signal $\Phi$ from the individual measured values. By comparison of the gradient with the calibration curve, it is then possible to determine the moisture content value of the sample.

Accordingly, this second mode of operation of the device permits the measurement of the empty resonator to be dispensed with. However, there is a requirement for multiple measurements on the same product of the same moisture content under differing density conditions. In the case of many pulverulent products, this is very readily possible, but this is also the case with products such as tobacco, cheese etc.

Figure 18:
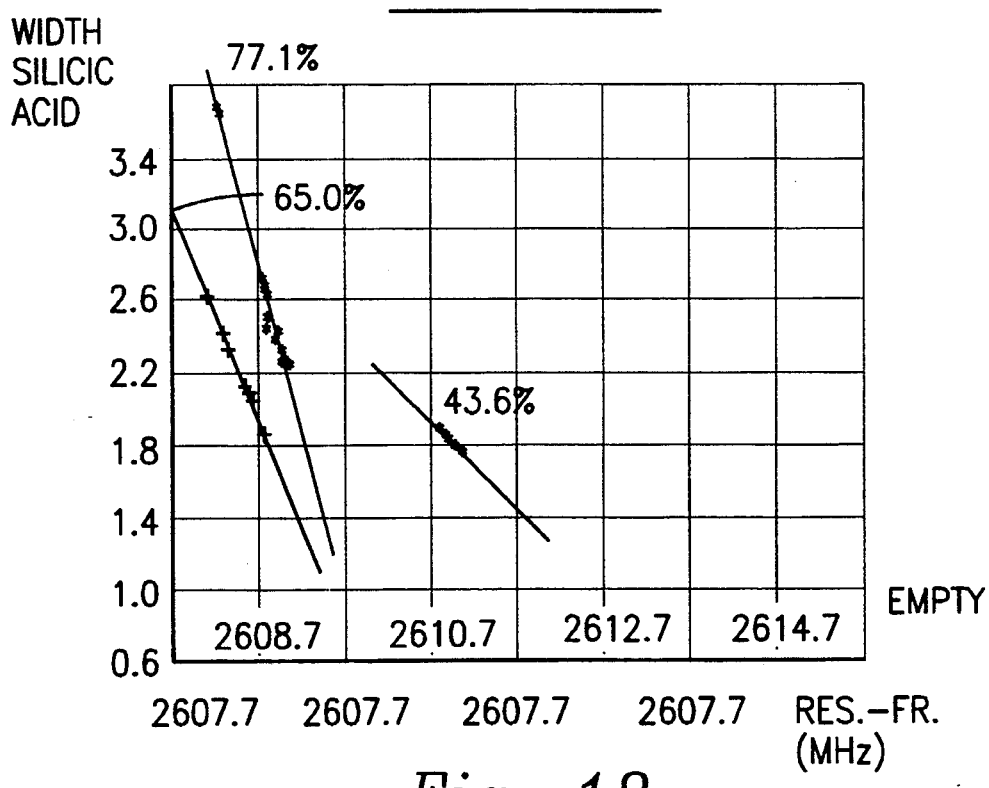

This process is of advantage if the empty condition of the resonator is constantly altering (e.g. very heavy contaminations due to the product), if an empty resonance measurement is not possible at all, because the product extends in a web, if the straight lines of constant moisture content (or of differing density) do not intersect one another at all at a point (FIG. 17 shows this for tobacco of high moisture content, i.e. over 20%, and FIG. 18 for silicic acid pressed material in the moisture content range up to 80%)

FIG. 17 shows the density independence in the case of moisture content measurement in tobacco by the microwave resonator method:

The straight lines of constant moisture content intersect one another at a point of the width/frequency diagram of the resonance data, in the case of this class of tobacco, only for moisture content values below 20%.

Accordingly, it would be possible to detect a density influence at over 20% moisture content when using the normal measurement method of the comparison of the empty and full resonator.

However, if the at multiple measurement of width and frequency under differing density conditions is employed for the measurement of the straight line gradient $\Phi(\rho)$, the density independence of the moisture content measurement is preserved up to extreme tobacco moisture contents exceeding 40%.

FIG. 18 shows, by way of example of a material under test such as silicic acid filler (moisture content range 40–80%) that the straight lines of constant moisture content in the width/frequency diagram have no common point of intersection whatsoever any longer, so that it is not possible to operate using the simple width/frequency measurement of the empty and filled resonator. On the other hand, by using the second mode of operation of the device, it is possible to determine the moisture-content-dependent process variable $\Phi$ reliably as the gradient of the straight line. In this manner, the measurement accuracy reaches $\pm 0.2\%$ up to 70% moisture content.

FIG. 19 shows, with reference to the example of a resonant frequency/width diagram for silicic acid in the lower moisture content range, the separation of the influence of moisture content and of density on the resonance signal.

The points of constant moisture content lie on a straight line having the gradient $\Phi = f(\psi) \neq f(\rho)$. Two methods are suitable for the determination of $\Phi$:

1. Comparison of width, frequency of resonance of the filled and empty resonator:

$$\Phi = b(o) - (b(Lo) + B \; (f(Lo) + F) - F(o)$$

2. Determination of the gradient of the regression line by a plurality of width/frequency points for a sample under differing density conditions.

In this case, it can clearly be seen how the signal $\Phi$ remains strictly density-independent when using this second mode of operation, where the gradient $\Phi$ of the straight line of constant moisture content in the width/frequency diagram is determined by differing compression conditions.

The second mode of operation can also be used for the moisture content measurement of incompressible materials. In this case, the measurements are made at differing levels of filling of the sample tube. The regression line and its gradient are then determined from the measured values of the differing filling-level conditions.

We claim:

1. A method for measuring the moisture content of a material under test using microwaves, in which method, under the control of a processor, an electromagnetic radiation of variable frequency is generated in a microwave generator and is fed to a sample applicator designed as a resonator, and in which the microwave signal emerging from the applicator is fed to a detector diode, from which signals b(O) and f(O) are determined as primary process variables by a computer via an analog/digital converter, where b(O) is the resonance half-width value at the resonance frequency f(O) of the applicator which is operatively connected to a test sample, whereby a material sample is brought into connection with the resonator so that an electric field extends generally parallel to the sample, and a null compensation for the detector diode is undertaken outside the resonance frequency f(O), the method further comprising the steps of calibration comprising the evaluation of samples of various material with known moisture content values $\Psi r$, using a measurement signal $\Phi(\Psi r)$ calculated as:

$$\Phi(\Psi r) = \frac{b(0) - b(L)}{f(L) - f(0)}$$

with b(L) and f(L) as constant material-dependent and applicator dependent reference quantities which are determined in accordance with the relations $$b(L) = b(LO) + B$$

$$f(L) = f(LO) + F$$

in which b(LO) and f(L0) are the half-width value and the resonance frequency respectively of the applicator without material under test and B and F are stored constants which are typical for the applicator and which are determined in a manner dependent upon the material to be measured, so that the measurement signal $\Phi(\Psi r)$ is independent of the packing density of the material and is dependent only upon the moisture content, and wherein disturbing influences of resonator contaminations and resonator temperature alterations are compensated by measurement and storage of b(LO) and f(LO) and recomputation of the measurement signal $\Phi(\Psi r)$.

2. A method for measuring the moisture content of a material under test using microwaves as recited in claim 1, wherein the determination of the measurement signal $\Phi(\Psi r)$ is performed by the use of calibration curves obtained by bringing a sample into connection with the resonator so that the electric field of the resonator extends generally parallel to the sample, wherein, for determination of the measurement signal $\Phi(\Psi r)$, being dependent from the material moisture content $\Psi r$ but independent from the material density, a sample material with constant moisture is introduced in different amounts into the electric field of the resonator, then for each different sample the resonance frequency and half-width value is measured and stored, then from the pairs of measuring points within the diagram of resonance frequency and half-width values a straight line of regression of the gradient is determined as moisture dependent measurement signal $\Phi(\Psi r)$, wherein during calibration of the resonator the moisture values of the sample of material are allocated to different values of the measurement signal $\Phi(\Psi r)$ and wherein then from the different calibration points of a $\Phi \times \Psi$ diagram a calibration curve is calculated and stored, and wherein the material moisture content $\Psi r$ of the sample is determined by comparison of the measurement signal $\Phi(\Psi r)$ measured by moisture measuring and the calibration curve.

3. A method as in claim 1, wherein an upstream microwave amplifier is set by the processor to effectuate the null compensation as to the power level of the resonance signal emerging from the resonator so that the diode operates at the same working point of maximum signal power whereby the maximum value of the resonance curve corresponds to a preselected value and thus diode nonlinearities have no disturbing effect on the measurement, the exact measurement points of the resonance curve are then plotted and the resonance frequency f(0) and half-width value b(0) are then determined from a polynomial interpolation of the resonance line measured values.

4. A method as in claim 1, wherein the test sample is introduced in the central regions of a circular-cylindrical or rectangular resonator parallel to the axis of the applicator, and wherein the E010 resonance or the H211 resonance or the H311 resonance is excited in the applicator in the case of the circular-cylindrical resonator, so that the electric field enters into the sample parallel to the sample.

5. A method as in claim 1, wherein the test sample, present in a form thinly rolled out or coated on a dielectric substrate or in the form of a thin layer, is introduced into the applicator along the E-field-parallel longitudinal axis of a circular-cylindrical or rectangular resonator and the fundamental resonance is excited, so that samples of arbitrarily high moisture content can be measured.

6. A method as in claim 2, wherein a thin large-area sample is conducted between the two halves of a circular-cylindrical or rectangular resonator cut open along the E-field-parallel longitudinal axis, and the fundamental resonance is excited.

7. A method as in claim 1, wherein a small part of the microwave power in the resonator is coupled out from a closed circular-cylindrical or rectangular resonator, in which the fundamental resonance is excited, via a coaxial line having the length of one quarter wavelength, and the sample is conducted through the stray field of the electromagnetic wave at the open end of the coaxial line so that the electric field lines enter into the sample parallel to the sample.

8. A method as in claim 1, wherein in the case of an ambiguity between the measurement signal $\Phi(\Psi r)$ and the material moisture content $\Psi r$ (maximum or minimum of the calibration curve) the measurement signals $\Phi 1$ and $\Phi 2$ are detected in two resonance modes of differing resonance frequency and the material moisture content is unambiguously determined so that the moisture content $\Psi R$ computed from the measurement signals $\Phi 1$ and $\Phi 2$ exhibits a minimal difference.

9. A method as in claim 2, wherein said method is carried out in a device comprising a microwave generator (3), which is digitally tunable by a processor (2), of variable frequency, which generator is connected to a coupling probe (5), which is disposed in an applicator (4) to measure the material moisture content $\Psi r$ of a sample (11), which applicator exhibits a further coupling probe (6), which is connected via an upstream microwave amplifier (7) to a detector diode (8), the signal output of which is connected to the processor (2).

10. A method as in claim 9, wherein the frequency of the microwave generator (3) can be set by means of a quartz-stabilized PLL control loop.

11. A method as in claim 9, wherein the applicator (4) is designed as a circular-cylindrical or rectangular resonator with a central passage, coaxial with the longitudinal axis (19), for the introduction of a sample (11), and a tube consisting of dielectric material for guiding the sample.

12. A method as in claim 9, wherein the applicator (4) comprises a closed cylindrical or rectangular resonator (22), through one end surface (23) of which the coupling probes (5, 6) are guided and through the other end surface (24) of which a coaxial line (18) is centrally guided, the free end portion (25) of the coaxial line is disposed in the region of the guide for the sample (11).

13. A method as in claim 9, comprising a measurement station (36) with an applicator (4) designed as a resonator (22), and an evaluation unit (26), between which two measurement lines (39, 40) and a control line (41) are disposed, the evaluation unit (26) comprising a display (34), u keyboard (35), an interface (38) for the connection of peripheral systems, a grid connection (37) and a bus (29) for a processor card (30), a terminal card (31), a microwave detector card (56), a microwave generator card (57), an input-output card (32) and an analog output (33).

14. A method as in claim 13, wherein the control line (41) is connected to a level probe (42) disposed in a sample tube (43) and a relay (48) for magnetic valves (46) of two shut-off components (44, 45), which are disposed in the sample tube (43) on both sides of the resonator (22) and are connected via the magnetic valves (46) to a compressed air or hydraulic line (47).

* * * * *